United States Patent
Zeigler

(10) Patent No.: US 7,018,804 B1
(45) Date of Patent: Mar. 28, 2006

(54) DETERMINATION OF CELL VIABILITY AND PHENOTYPE

(75) Inventor: Francis C. Zeigler, Encinitas, CA (US)

(73) Assignee: Orion Biosolutions, Inc., Vista, CA (US)

( * ) Notice: Subject to any disclaimer, the term of this patent is extended or adjusted under 35 U.S.C. 154(b) by 0 days.

(21) Appl. No.: 11/075,644

(22) Filed: Mar. 8, 2005

Related U.S. Application Data

(60) Provisional application No. 60/633,115, filed on Dec. 3, 2004.

(51) Int. Cl.
*G01N 33/50* (2006.01)

(52) U.S. Cl. .................... 435/7.1; 435/29; 435/40.5

(58) Field of Classification Search ............... None
See application file for complete search history.

(56) References Cited

U.S. PATENT DOCUMENTS

| | | |
|---|---|---|
| 6,403,378 B1 | 6/2002 | Phi-Wilson et al. |
| 6,777,233 B1 | 8/2004 | Carpenter |

OTHER PUBLICATIONS

Martinat, Cecile, et al. "Sensitivity to Oxidative Stress in DJ-1-Deficient Dopamine Neurons: An ES-Derived Cell Model of Primary Parkinsonism", *PLoS Biol.* (2004) 2(11):1754-1763.

Herzenberg, Leonard A., et al. "The History and Future of the Fluorescence Activated Cell Sorter and Flow Cytometry: A View from Stanford", *Clinical Chemistry* (2002) 48(10):1819-1827.

Van De Loosdrecht, A.A., et al. "A tetrazolium-based colorimetric MTT assay to quantitate human monocyte mediated cytotoxicity against leukemic cells from cell lines and patients with acute myeloid leukemia", *J. Immunol Methods,* (1994) 174(1-2):311-320.

Ohno, M., et al. "Rapid colorimetric assay for the quantification of leukemia inhibitory factor (LIF) and Interleukin-6 (IL-6)" *J. Immunol. Methods.* (1991) 145(1-2):199-203.

Ferrari, M., et al. "MTT colorimetric assay for testing macrophage cytotoxic activity in vitro", J. Immunol. Methods (1990) 131(2):165-172.

Alley, M.C., et al. "Feasibility of drug screening with panels of human tumor cell lines using a microculture tetrazolium assay", *Cancer Res.* (1988) 48(3):589-601.

Carmichael, J., et al. "Evaluation of a tetrazolium-based semiautomated colorimetric assay: assessment of radiosensitivity", *Cancer Res.* (1987) 47(4):943-946.

Gerlier, D., et al. "Use of MTT colorimetric assay to measure cell activation", *J. Immunol. Methods* (1986) 94(1-2);57-63.

Mosmann, T. "Rapid colorimetric assay for cellular growth and survival application to proliferation and cytotoxicity assays", *J. Immunol Methods* (1983) 65(1-2):55-63.

*Primary Examiner*—James Ketter
(74) *Attorney, Agent, or Firm*—Townsend and Townsend and Crew, LLP

(57) ABSTRACT

This invention provides methods to the determination of the viability of the cell by a first reagent and the phenotype of a cell by use of one or more second reagent. The first reagent is one that is detectable in viable, or living, cells even after they have been fixed such that they are no longer viable. The one or more second reagent is compatible for use in fluorescence activated cell sorting (FACS) including intracellular FACS. The invention thus provides methods of simultaneously identifying a cell as both viable and having a phenotype of interest. The invention also provides compositions for use in the disclosed methods.

20 Claims, 1 Drawing Sheet

DETERMINATION OF CELL VIABILITY AND PHENOTYPE

RELATED APPLICATIONS

This application claims benefit of priority from Provisional U.S. Patent Application 60/633,115, filed Dec. 3, 2004, which is hereby incorporated in its entirety as if fully set forth.

FIELD OF THE INVENTION

This invention relates to the determination of the viability of the cell by a first reagent and the phenotype of a cell by use of one or more second reagent. The first reagent is one that is detectable in viable, or living, cells even after they have been fixed such that they are no longer viable. The one or more second reagent is compatible for use in fluorescence activated cell sorting (FACS) including intracellular FACS. The invention thus provides methods of simultaneously identifying a cell as both viable and having a phenotype of interest. The invention also provides compositions for use in the disclosed methods.

BACKGROUND OF THE INVENTION

Fluorescence activated cell sorting (FACS) is a powerful method that has been used to identify cells having a particular phenotype. See Herzenberg et al. (*Clincal Chem.* 48(10):1819–1827 (2002)) for a review. In some forms, the FACS method has been used in combination with monoclonal antibodies as a reagent to detect cells as having a particular antigen, which is usually indicative of an expressed protein. The method has been used extensively in relation to antigens expressed on the surface of cells, including cells that remain alive during, and after, FACS. Similarly, the method has been used with intracellular reporter gene systems based on the expression of a detectably labeled gene product by the cell.

The method has also been used to detect contents within fixed cells via an alternative form of intracellular FACS. This method permits the detection of intracellular molecules that are not expressed in a labeled form by first fixing the cells followed by permeabilization of the cells to permit entry of a reagent, like an antibody, that binds an intracellular factor. Of course the use of fixation kills all cells in a sample. Thus this intracellular FACS method does not permit the separate identification of viable cells that contain an intracellular molecule from dead, or dying, cells containing the same molecule. This is despite a variety of means and methods known in the field to determine cell viability.

Approaches to determine cell viability are based on the principle of viable cells being capable of excluding certain agents, such as trypan blue and ethidium monoazide. Trypan blue staining for example, is based on cell membrane integrity, which is utilized based upon a presumed correlation to cell death, which permits entry of the dye. Other approaches are based on the principle of viable cells taking up reagents or factors that can be used to identify the cells as having been alive. Examples of this approach include the uptake of radioactive substances, such as tritium-labeled thymidine, or the uptake of a tetrazolium salt, such as the yellow tetrazolium salt MTT, which is enzymatically reduced by dehydrogenases to form insoluble purple formazan crystals by the mitochondria in metabolically active cells. The crystals are solubilized by the addition of an organic solvent, such as isopropyl alcohol or dimethyl sulfoxide, to permit color detection by spectrophotometric means. Unfortunately, the solvents used in a MTT based assay also lyse the cells to result in an overall amount of color to determine the number of viable cells.

References discussing the above methods include van de Loosdrecht, A. A., et al. J. Immunol. Methods 174: 311–320, 1994; Ohno, M., and T. Abe. J. Immunol. Methods 145: 199–203, 1991; Ferrari, M., et al. J. Immunol. Methods 131: 165–172, 1990; Alley, M. C., et al. Cancer Res. 48: 589–601, 1988; Carmichael, J., et al. Cancer Res. 47:936–42, 1987; Gerlier, D., and N. Thomasset. J. Immunol. Methods 94: 57–63, 1986; and Mosmann, T. J. Immunol. Methods 65: 55–63, 1983.

U.S. Pat. No. 6,403,378 describes a method based on membrane integrity that utilizes two dyes, one of which labels all intact cells while the other labels all dead cells. The methodology permits all non-viable cells to be detected at one wavelength while all viable and non-viable cells can be detected at a different wavelength.

Citation of documents herein is not intended as an admission that any is pertinent prior art. All statements as to the date or representation as to the contents of documents is based on the information available to the applicant and does not constitute any admission as to the correctness of the dates or contents of the documents.

BRIEF SUMMARY OF THE INVENTION

This invention provides methods and compositions for the use of a first reagent and one or more second reagents to identify cells as being both viable and having a phenotype of interest. The first reagent is a pre-dye to detect viable cells based upon the presence of oxidative metabolism, or the redox environment that results, in cells that are alive. The viable cells may be present within a larger population of cells containing both living and dead cells. Thus the presence of the detectable dye may be directly correlated to the number of viable cells tested. Therefore, a direct determination of cell number and detectable dye permits an accurate and straightforward quantification of viable cells.

The one or more second reagent is used to detect the presence of one or more molecules which are indicative of a cell's phenotype. The molecules may be present on the surface or inside a cell. Alternatively, and where more than one molecule is involved, they may be found both on the surface and inside a cell. The one or more second reagent detects the molecule(s) by binding thereto.

The invention thus provides a method to identify a cell as viable and having a particular phenotype by contacting the cell with a pre-dye first reagent which is converted to a detectable dye in the redox environment of a viable or living cell. Preferably, the pre-dye is converted due to the presence of oxidative metabolism, such as by reaction with a reactive oxygen species (ROS) as a non-limiting example, in viable cells. Contacted cells are fixed such that viable cells remain stained by the converted, and now detectable, dye. Detection of the dye in fixed cells identifies them as having been viable prior to the fixing step. Preferably, the pre-dye is converted into a dye that is detectable based on its fluorescent properties (i.e. ability to absorb light at one wavelength and then emit, or fluoresce, light at a higher wavelength).

The fixed nature of the detectable dye and the cell advantageously provide stability in the cells such that further processing may be delayed if desired. This reflects a distinct benefit over situations wherein the dye and/or cells are not fixed, in which cases the cells must be evaluated without significant delay.

The fixed cells are contacted with one or more second reagent used to detect a phenotype of interest. The phenotype is indicated by the presence of one or more molecules found in or on the cells. To detect an extracellular molecule indicative of a phenotype, the second reagent may be used without permeabilization of the fixed cells. Where an extracellular molecule is actively synthesized, the molecule can also be detected while being synthesized intracellularly. Stated differently, an extracellular molecule can be detected intracellularly while it is being synthesized, and before it is present at the cell surface. Alternatively, an extracellular molecule can be detected prior to fixation and subsequent permeabilization of a cell. This permits the identification of molecules only on the cell surface without inclusion of intracellular forms of the molecule (like those being synthesized). To detect an intracellular molecule, the cells are preferably permeabilized prior to contact with the second reagent.

The relationship of a second reagent to the cellular molecule to which it binds may be characterized more generally as that of two members of a specific binding pair. In this relationship, the first member of the pair that binds to allow detection of the cellular molecule, which is the second member of the pair that, when present in a cell, is indicative of a particular phenotype.

The presence of both the first and second reagents in a cell thus identifies the cell as both having been viable and having a particular phenotype. The presence of the reagents may be by detection of fluorescence from the first reagent and detection of the second reagent bound to a cellular molecule indicative of the phenotype. In many embodiments of the invention, the detection may be performed by analyzing and/or sorting the cells by dual-parameter fluorescent activated cell sorting (FACS). In situations where more than one second reagent is used, the use of multi-parameter FACS is preferred. Herzenberg et al. (*Clincal Chem.* 48(10):1819–1827 (2002)) describe the use of 12 fluorescent colors and 2 scatter parameters in 2002.

Thus, the methods of the invention may be used to determine the number of cells that are both viable and that possess a particular phenotype in any cell containing sample, including samples that are a representative portion of a larger population of cells. The invention may thus be used to determine the number, or more importantly the relative number, of cells that are both viable and of a particular phenotype within a larger population of cells. This may be advantageously applied to the determination of viable cells of a particular phenotype in a population of cells for use in transplantation as discussed herein. Such cells include cells to be introduced, or re-introduced, into a subject.

The ability to practice the invention in combination with FACS offers significant benefits in the simultaneous detection of viability and one or more phenotypes. The consideration of situations where viability and one phenotype as a non-limiting example illustrates that a plurality of cells used in the practice of the invention may be differentiated, or sorted, into four separate categories. The first category are cells that were both viable and possessing of the detected phenotype (i.e. stained by both reagents) while the second category are cells that were viable but did not possess the phenotype (i.e. stained by the viability detecting dye but not the second reagent). The third category are cells that were not viable but did possess the detected phenotype (i.e. not stained by the viability detecting dye but stained by the second reagent, while the fourth category are cells that were not viable and did not possess the phenotype (i.e. not stained by either reagent). The use of additional second reagents to detect additional phenotypes permit the differentiation of a plurality of cells into additional groups. For example, the detection of viability and two phenotypes can result in eight categories (each of the four described above divided into two, for a total of eight, based upon the presence or absence of the second phenotype).

This ability to differentiate a single plurality of cells is not available in the use of agents that detect cell viability based upon entry into dead cells via a leaky cell membrane, which rely heavily on the presumption that cells not so labeled are viable. The presumption is particularly dangerous because of the likely presence of non-viable cells with an intact or relatively intact cell membrane. The ability to differentiate cells into four categories is particularly advantageous in situations where the effect of a procedure or treatment, including contact with a test compound or drug, is used performed as described herein because the effects on viability and the one or more phenotypes can be separately detected and analyzed.

The invention also provides a method to determine the relative number of viable cells having a particular phenotype in a population of cells by first contacting a portion, or other representative sample, of said population of cells with a pre-dye wherein said pre-dye is converted to a detectable dye in the redox environment of a viable or living cell as described above. The contacted cells are then fixed such that viable cells remain stained by the converted, and now detectable, dye. Fixed, dye-labeled, cells are then optionally permeabilized and contacted with one or more second reagent as described above to detect one or more cellular molecule indicative of a phenotype.

The cells are then detected and used to determine the number of viable cells having the phenotype indicated by the cellular molecule(s) bound to one or more second reagent. The detected cells may be treated as a representative sample of said population of cells, based on the number of cells stained with both reagents in comparison to the total number of cells in the portion. Preferably, the pre-dye is converted into a dye that is detectable based on its fluorescent properties. The second reagent may be detected directly, if it is detectably labeled, or detected indirectly, such as if an additional reagent is necessary to render the label detectable. Preferably, the second reagent is detectably labeled with a fluorescent marker, especially when more than one second reagent are used in the practice of the invention.

The invention is advantageously used in cases of cells or tissues destined for transplantation, whether autologous or otherwise, where the testing of both viability and desired therapeutic phenotype (or phenotype of interest) of a sample of the cells or tissue provides valuable information as to the likelihood of success in using the cells in transplantation. Non-limiting examples include the testing of cells for insulin production as the desired phenotype for transplantation into a subject with diabetes and testing of cells for dopamine production as the desired phenotype for use in a subject with Parkinson's disease. The invention can also be used to evaluate the likelihood of success in using one source of donor cells or tissues versus another based upon the number or percentage of viable cells having the therapeutically desired phenotype in each donor source.

Alternatively, the invention may be used to determine the number or percentage of viable cells with a desired phenotype in a "seed" culture used to inoculate a larger culture or fermentation batch. In the case of large scale fermentation of mammalian or primate or higher eukaryotic cells, the cost of the media is significantly high such that the ability to identify a "seed" culture as having larger numbers of viable cells with the phenotype of interest provides the benefit of avoiding the use of poor "seed" cultures. For example, the use of higher eukaryotic cells in an expression system to produce a protein recombinantly can benefit from the use of the present invention to identify the numbers of viable cells that express the protein.

The methods may also be used to detect simultaneously the effects of various procedures on cell viability or proliferation and a phenotype. Thus a treatment may be applied to a population of cells followed by a determination of the effect of the treatment on cell viability and phenotype. Non-limiting examples of this additional aspect of the invention include the use of the methods disclosed herein to determine drug sensitivity, cytotoxicity of a test compound, cellular response to growth factors, and cell activation. All of these parameters may be evaluated with respect to viability and effect on phenotype, independently or in combination.

This aspect of the invention may be applied to test a molecule for the ability to modulate oxidative insult which alters the redox environment within a cell. Thus the invention may be used to identify an agent as causing oxidative insult or a molecule as able to reduce or alleviate oxidative insult in the presence of a second agent that causes oxidative insult. Embodiments of this aspect of the invention include the identification of an agent that may cause oxidative insult related to Alzheimer's disease and Parkinson's disease as non-limiting examples. With respect to the latter, the invention may be used with molecules that may be involved in the degradation of dopamine producing neuronal cells. Of course the invention can also be used to identify an agent as reducing or alleviating oxidative insult in any of these conditions.

The details of one or more embodiments of the invention are set forth in the accompanying drawings and the description below. Other features, objects, and advantages of the invention will be apparent from the drawings and detailed description, and from the claims.

MODES OF PRACTICING THE INVENTION

Figure 1:
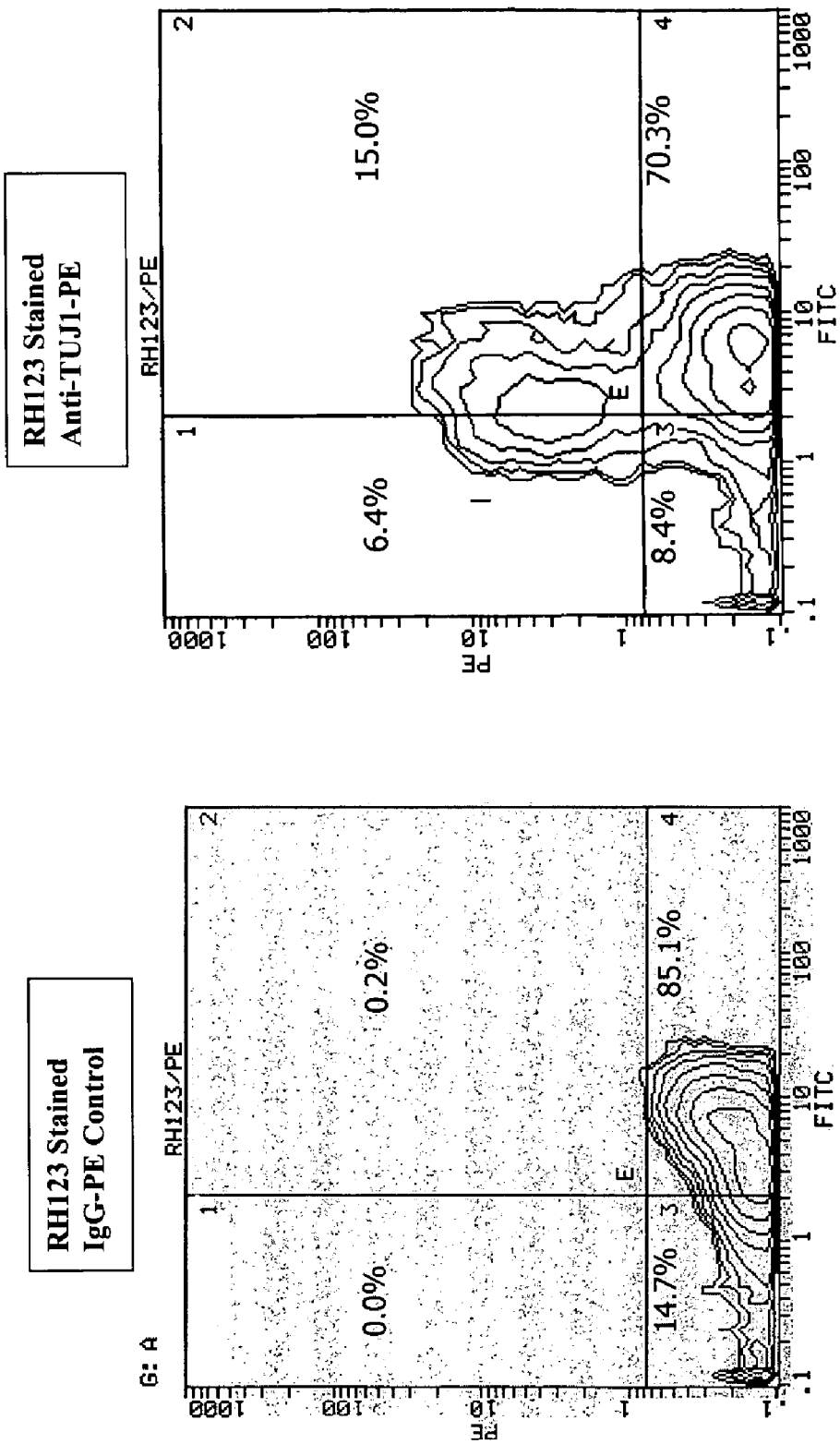
FIG. 1 shows the results of intracellular FACS analysis of rat neural stem cells for viability and beta-tubulin III (TuJ1) expression.

This invention provides a method of identifying a cell as having been viable and as having had a phenotype of interest, said method comprising contacting a cell with an amine containing pre-dye wherein said pre-dye is converted to a detectable dye in viable cells; fixing the contacted cell such that cells that were viable remain stained by the dye; optionally treating the fixed cells with a permeabilizing agent; contacting the cells with a labeled first member of a binding pair which binds to a second member of the binding pair in or on said fixed cells, wherein presence of said second member is indicative of a cell with a phenotype of interest; and identifying said fixed cell as having been viable and having said phenotype by detection of fluorescence from said dye and detection of said labeled first member bound to said second member.

As used herein, the term "viable" refers to cells that maintain homeostasis by the use of one or more energy consuming mechanisms. Thus a "viable" cell includes those in which productive oxidative metabolism occurs to produce the necessary energy; those in which only glycolysis is used to produce energy, as well as those which maintain cellular integrity, such as the ability to exclude, or actively remove, certain molecules from the interior of the cell, by energy consuming mechanisms. Preferably, a "viable" cell is capable of undergoing mitosis, cell growth, differentiation, and/or proliferation. Of course a "viable" cell is synonymous with a "living" cell, which includes cells that are quiescent (and thus not going through the cell cycle), but nonetheless alive because energy production and consumption occurs in such cells to maintain homeostasis.

The invention also provides modifications of the above, such as the use of more than one labeled first members, which bind to a corresponding number of more than one second members, wherein each first member binds its corresponding second member to form a binding pair. One member of each pair is labeled as described herein, preferably with a fluorescently detectable label as described by Herzenberg et al. (*Clincal Chem.* 48(10):1819–1827 (2002)). The corresponding second member of each pair is found in or on a cell used in the practice of the invention. With the use of one first member, the invention is preferably performed with the identification of cells by use of two channel fluorescent activated cell sorting (FACS).

The members of a binding pair are preferably members of a specific binding pair, wherein one member of the pair has an area on the surface or in a portion thereof which specifically binds to the other member of the pair. A member of a pair may thus be viewed as having a particular spatial and/or local organization that permits binding, or specific binding in the case of a specific binding pair, to the other member of the pair.

The members of a pair may be referred to as ligand and anti-ligand (or receptor), either of which may be the first member of the pair. In some non-limiting embodiments of the invention, the two members of a pair will be immunologically related such as in an antigen and antibody relationship wherein the antigen is the ligand and the antibody is the anti-ligand or receptor. Other such embodiments include the use of two cell surface binding molecules as the members of the pair.

Other non-limiting pairs include biotin and avidin (or streptavidin); hormone and hormone receptor; two complementary nucleic acid molecules (such as a genomic sequence and a probe sequence, including DNA and DNA, DNA and RNA, DNA and PNA, RNA and DNA, RNA and PNA as well as RNA and RNA); nucleic acid molecule and nucleic acid binding dye; immunoglobulin and protein A; phosphorylated serine residues and annexin; thiol moieties and Alexa 594 maleimide (ALM); as well as cellular target and small organic molecule (such as a drug compound). PNA refers to peptide nucleic acids, or other arrangement of nucleotide bases by use of a peptide based backbone.

With respect to antibodies used as a labeled first member of a pair (or immunophenotyping), the invention provides for the use of any immunoglobulin, or derivative or fragment thereof, which functions as the first member to bind the second member of the pair. Thus the antibody may be monoclonal, polyclonal, hybrid or chimeric, single chain, an $F_{ab}$ fragment, $F_v$, or single chain $F_v$. The labeled first member of a pair may also be viewed as any reagent that may be used in immunohistochemistry based detection of a cellular molecule or antigen, including tumor antigens (expressed in correlation with tumor status or type).

In many embodiments of the invention the second member of the pair is a cellular molecule to be detected based on its suitability to serve as an indicator of a cellular phenotype.

Thus in preferred embodiments of the invention, the second member is an RNA (or mRNA) molecule or sequence; a polypeptide; or a DNA molecule or sequence. The second member may be a cellular molecule that is not endogenous to the cell, such as, but not limited to, a molecule that is present in or on a cell due to infection with a pathogen, including viruses and fungi. In such cases, the second member is indicative of the infection with the pathogenic agent. Non-limiting examples include viral envelope or capsid proteins, viral enzymes (such as polymerases, reverse transcriptases, and proteases), and viral regulatory proteins (such as the TAT, REV, or NEF proteins of HIV). To detect RNA or DNA, the first member is preferably a detectably labeled nucleic acid probe that is complementary to the RNA or DNA to be detected. To detect a polypeptide as a ligand present in or on a cell, any appropriate anti-ligand may be used. Preferred in the practice of the invention is the use of an antibody that binds the polypeptide.

When the second member is the cellular molecule, the first member is labeled in the use of the invention. While the first member may be detectably labeled, such as with a fluorescent marker having a functionally distinct emission spectra from the detectable dye used to detect viability (as well as other fluorescent markers that may be used in situations with multiple first and second members as described herein), the first member may also be labeled for indirect detection. Non-limiting examples of fluorescent markers include phycobiliproteins (phycoerythrin or PE and allophycocyanin or APC), Cy5PE, Cy7PE, Cy7APC, Cy5, fluorescein (FITC), Texas Red (TR), and Cascade Blue.

Non-limiting examples of a first member labeled for indirect detection include those labeled with an enzyme or biotin such that a secondary agent is used to detect the labeled first member. In the case of an enzyme label, the secondary agent may be a substrate for the enzyme; with biotin, the secondary agent may be detectably labeled streptavidin. Antibodies may also be used without a label but with a secondary agent such as by use with detectably labeled protein A, or a detectably labeled secondary antibody, to detect an antibody first member bound to a second member of a binding pair. A non-limiting example of a secondary antibody is an anti mouse IgG, goat $F(ab')_2$ that is Fc gamma fragment specific in cases where detection of a mouse IgG is needed.

The second member of a pair is found within a cell or on the cellular surface and is a molecule the presence of which is indicative of a phenotype of interest. Non-limiting examples of intracellular molecules detected with use of the invention include thioredoxin, cytokines, interleukins, interferons, insulin, dopamine, tyrosine hydroxylase or another enzyme, structural proteins (such as microtubules, intermediate filaments, and actin fibers), regulatory proteins, steroid hormone receptors; and other intracellular antigens. Non-limiting examples of cell surface molecules detected with use of the invention include the various CD markers, including CD4, CD8, CD34, CD49f, CD133, CD105, and CD38; integrins; immunoglobulin superfamily cell adhesion molecules (such as ICAM and NCAM); membrane channels; cell surface receptors; and other cell surface molecules or markers, including those used in FACS to identify immune system cell types as well as cells of the hematopoietic lineage.

Other exemplars of the second member include include those indicative of insulin producing cells, pancreatic islet cells (including alpha cells or beta cells or exocrine or ductal cells), peripheral blood mononuclear cells (PBMCs) or types thereof, dopamine producing cells, hepatocytes, neurons, motor neurons, glial cells, lymphocytes (including B cells and T cells), leukocytes, monocytes, granulocytes (neutrophils, eosinophils, basophils), phagocytes, fibroblasts, skin cells, hair cells, epithelial cells, oligodendrocytes, hematopoietic stem cells, mesenchymal stem cells, chondrocytes, keratinocytes, endothelial cells, smooth muscle cells, macrophages, hepatocytes, neural stem cells, pancreatic stem cells, astrocytes, oligodendrocytes, 3T3 cells, 293 cells, COS cells, CHO cells, MEF (mouse embryonic fibroblasts), or HUVEC (human umbilical vein endothelial cells), CaCo-2.

Phenotypes of interest include any phenotype that may be possessed by a cell of the invention, including the following non-limiting examples: expression of a particular gene product (endogenous or not), including both nucleic acid molecules and polypeptides; presence of a metabolite, including lipids and carbohydrates; and the expression of a therapeutically effective amount of a cellular molecule, such as production of insulin or dopamine. Cells that possess a therapeutically effective phenotype include cells that have been recombinantly engineered in vitro or ex vivo for use in the treatment of disease and undesirable conditions. Non-limiting examples include cells used as monovalent or polyvalent vaccines, including cancer vaccines and cells to stimulate the immune response to antigens. The invention contemplates the use of the invention with cells used in the treatment of viral infections, fungal infections, and genetic diseases.

The invention also provides a method of determining the number, or the relative number, of viable cells having a phenotype of interest in a population of cells, said method comprising contacting a portion of the population of cells with an amine containing pre-dye wherein said pre-dye is converted to a detectable dye in viable cells; fixing the contacted portion of cells to form fixed cells wherein cells that were viable remain stained by the dye; optionally treating said fixed cells with a permeabilizing agent; contacting said fixed cells with a labeled first member of a binding pair which binds to a second member of the binding pair in or on said fixed cells, wherein presence of said second member is indicative of a cell with a phenotype of interest; and determining number, or the relative level of, viable cells having the phenotype in said portion, as a representative sample of said population of cells, based on the number of cells stained with said fluorescent dye and bound by the labeled first member via the second member in or on the cells, in comparison to the total number of cells in said portion.

In determining the relative number of cells, the number of cells detected as being both viable and having the phenotype are compared to the total number of cells in the contacted portion or the number of number of cells that were not so doubly detectable. This can also be used to determine the percentage of cells that are viable in the tested sample, and thus the original population of cells.

The contacting of a cell with a pre-dye may be performed at any point prior to fixation of the cell. Non-limiting examples include addition of the pre-dye to cells, tissues, or organs, after surgical removal and during disruption of the cells (or other means of isolation and/or treatment), such as by enzymatic digestion. Thus the pre-dye may be present during contacting of the cell with collagenase and/or trypsin. In some preferred embodiments of the invention, the cells are contacted with pre-dye immediately prior to, or shortly before, fixation, to identify cells as viable just before fixation.

The conversion of the pre-dye to a detectable dye in viable cells results from a chemical reaction favored by the redox environment of a living cell. This environment includes contributions to metabolic activity by mitochodria, as reflected by mitochondrial enzymes and activities. The term "redox environment" is used in relation to a system, such as that within a viable cell or tissue, that has many linked redox couples. A redox couple refers to the oxidized and reduced molecular forms that give rise to the couple. A non-limiting example is seen in the case of NAD+ and NADH, which are a redox couple that can be used to define a redox state based on the ratio of free NAD+ to free NADH. Another example of a redox couple, or pair, is glutathione disulfide (GSSG) and two molecules of glutathione (GSH). Another way to define redox state is by the half-cell reduction potential and the reducing capacity of that couple.

A redox environment is a summation of the products of the reduction potential and reducing capacity of the linked redox couples, such as that found in an organelle, a cell, a tissue, or a biological fluid, that are present. See Schafer F Q, Buettner G R. (2001) Redox state of the cell as viewed through the glutathione disulfide/glutathione couple. *Free Radic Biol Med.* 30:1191–1212.

This environment normally reflects the presence of oxidative metabolism in the cell, which may include the presence of a reactive oxygen species (ROS) in the cell. Non-limiting examples of ROS include singlet oxygen, hydrogen peroxide, and nitroperoxides, which are produced in viable cells. The invention also contemplates the production of ROS in living cells due to reactions other than oxidative metabolism, such as via catabolism or even anabolic activity. Oxidative metabolism refers to cellular processes which are utilized to produce energy, such as in the form of ATP or NADH or NADPH, which results in a redox environment that converts a pre-dye to a detectable dye.

The term "pre-dye" refers to a molecule which is not readily detectable and which can be converted to a "detectable dye" under appropriate conditions, such as those of the redox environment within a viable cell. Preferably, a "pre-dye" of the invention contains an amine, more preferably a primary or secondary amine, group. Alternatively, a "pre-dye" may contain a group which is converted to an amine group, such as a primary or secondary amine, within a viable cell prior to, or along with, a conversion of the "pre-dye" to a detectable dye.

A "detectable dye" is a molecule which is readily detected either directly or indirectly, preferably by virtue of its fluorescence characteristics, and which is created upon conversion of its corresponding "pre-dye" under conditions such as those within a living cell. Non-limiting examples of a "pre-dye" include non-fluorescent dihydrorhodamine 123 (CAS 109244-58-8), which is converted to fluorescent rhodamine-123 in a living cell; MTT (CAS 298-93-1,3-(4, 5-dimethylthiazol-2-yl)-2,5-diphenyltetrazolium bromide); and XTT (CAS 111072-31-2,2,3-bis-(2-methoxy-4-nitro-5-sulfophenyl)-2H-tetrazolium-5-carboxanilide). The "detectable dye" of the invention contains an amine group, preferably a primary amine group, which can be used to fix or crosslink the dye within a cell without deleterious effect on the detectability of the dye. A preferred pre-dye of the invention is dihydrorhodamine 123.

A range of effective concentrations or amounts of the pre-dyes may be used in the practice of the invention depending upon the number, nature, and form of the cells being assayed, the nature of the pre-dye selected for use, and the conditions used in the practice of the invention. All of these factors, however, can be readily adjusted by the skilled person to determine a variety of effective concentrations or amounts, which are suitable for the detection of viable cells as described herein. Accordingly, no single range of concentrations can be stipulated for use with all cell types. As a non-limiting example offered for a better understanding of the invention, however, a range of about 100 nM to about 1, about 5 or about 10 or 100 µM, final concentration, of dihydrorhodamine 123 may be used in the practice of the invention with many cell types, including fibroblasts, epithelial cells, and neuronal cells. Thus use of dihydrorhodamine 123 at concentrations of about 100 about 200, about 300, about 400, about 500, about 600, about 700, about 800, and about 900 nM as well as about 2, about 3, about 4, about 5, about 6, about 7, about 8, about 9, about 10, about 20, about 30, about 40, about 50, about 60, about 70, about 80, about 90, and about 100 µM are contemplated for use in the practice of the invention with from about $10^5$ to about $10^6$ or $10^7$ cells. Higher concentrations are preferred for use if cells exceed $10^7$ in number. Of course the use of a higher concentration permits the use of a relatively shorter period of time in comparison to a lower concentration, which would be used for a longer period of time.

The fixing of cells containing a detectable dye as disclosed herein is preferably by use of a fixative containing an aldehyde, such as, but not limited to, formaldehyde, paraformaldehyde, glutaraldehyde, and acrolein. Non-limiting examples of such fixatives include formalin and other formaldehyde containing compositions. The use of an aldehyde is complementary to the amine, preferably a primary amine, group present in the detectable dye used in the invention because the aldehyde is capable of crosslinking the dye to other cellular components. The use of formaldehyde is preferred for the practice of the invention. Glutaraldehyde, optionally at lower concentrations or with subsequent quenching of unreacted aldehyde groups (such as with reducing agents like sodium borohydride, or by reaction with exogenous amine-containing reagents like ammonium chloride or glycine) which fluoresce, may also be used. Preferably, however, the fixative does not contain red blood cell (RBC) lysing agents.

In addition to formalin, other fixatives containing formaldehyde may be used in the practice of the invention. Such fixatives preferably contain additional agents to stabilize or extend the shelf-life of the formaldehyde. Preferably, such fixative combinations are prepared as a concentrated solution that is diluted prior to use. Non-limiting examples of such combinations as a concentrated stock include C1–C6 alcohols (from about 5 or about 10 to about 15 or 20% by weight), optionally with C1–C6 acids (about 0.1 to about 0.5% by weight), in the presence of about 37–40% (by weight) formaldehyde. The base solution for diluting fixatives may be PBS, as a non-limiting example.

After fixation, the cells are preferably permeabilized with a permeabilization agent. Permeabilization is necessary where phenotype detection includes use of a second reagent (first member of a binding or specific binding pair) that binds an intracellular molecule. The permeabilization may also serve to remove unbound or excess dye from the cells. The cells are preferably permeabilized with a non-ionic detergent or surfactant as needed. Non-limiting examples of such detergents include Tween-20 (polyoxyethylene-sorbitan monolaurate), sapoinin, and Triton X-100. Using Tween-20 as a non-limiting example, the detergent concentration may be from about 0.01% to about 1%. Thus the invention includes use of detergents at about 0.01%, about 0.05%, about 0.1%, about 0.2%, about 0.3%, about 0.4%, about 0.5%, about 0.6%, about 0.7%, about 0.8%, about 0.9%, or about 1%. The detergent or surfactant may be in a base solution of PBS, optionally with sodium azide (as a preservative), as a non-limiting example. Other permeabilization agents include IntraCyte-Wash™ (IntraCyte Kit from Orion Biosolutions, Inc., Vista, Calif.) or FACS Permeabilizing Solution (Becton Dickinson Biosciences), both of which may be used according to the manufacturer's instructions.

Also after fixation, the cells may be treated by addition of a blocking agent prior to contact with a labeled first member of a binding or specific binding pair. The blocking agent is preferably non-specific binding material, such as non-fat dried milk or bovine serum albumin (BSA), at concentrations such as from about 0.01% to about 1, 2 or 3 or 4 or 5% in PBS. Thus the invention includes use of a blocking agent at about 0.01%, about 0.05%, about 0.1%, about 0.2%, about 0.3%, about 0.4%, about 0.5%, about 0.6%, about 0.7%, about 0.8%, about 0.9%, about 1%, about 1.5%, about 2%, about 2.5%, about 3%, about 3.5%, about 4%, about 4.5%, or about 5%. The blocking agent is preferably used where the labeled first member is likely to produce significant background signals (resulting in loss of signal to noise ratio) when the blocking agent is not used. When blocking agent is used, the cell containing mixture may be incubated in the dark for 30 minutes or more as a non-limiting example.

In the practice of the invention, the cells are either in suspension or made to be in suspension, such as, but not limited to, by enzymatic digestion or dissociation, prior to fixation. This permits the advantageous ability to identify, or detect, cells labeled by the detectable dye via use of fluorescent activated cell sorting (FACS). This is a preferred embodiment of the invention because it provides the ability to detect and count the number of cells expeditiously. Alternatively, the cells in suspension may be analyzed by use of a traditional hemacytometer. In another embodiment, the cells may be analyzed directly, such as in the case of adherent cells which are treated as described herein and then used to detect the number of cells stained with a detectable dye.

In the practice of the invention with use of FACS, a sample of cells may be combined (or "spiked") with an amount of detectable beads or particles for use as a positive control. The beads or particles can be used to determine the absolute number of counts for use in reference to the sample of cells being assayed.

Cells that may be used in the practice of the invention include any eukaryotic cell, including those isolated from a living or recently deceased subject, which may be labeled by the pre-dye/detectable dyes of the invention. Non-limiting examples include human or other mammalian (e.g. mouse or rat) or primate cells as well as a primary isolate of cells or tissues. In one embodiment of the invention, the cells are in a donor tissue or organ from one subject intended for use in a different (recipient) subject or for re-introduction into the donor. The cells may have been isolated by any appropriate method, including, but not limited to, surgical techniques to isolate cells and/or tissues. The populations of cells used in the practice of the invention include populations of any cell described herein, including populations containing insulin producing cells and dopaminergic neuronal cells.

Cells used in the present invention may also have been previously cultured in vitro or ex vivo (such as by use of tissue culture medium) prior to being use in the methods of the invention. The culture method or means may be any known or accepted in the art, so long as they are suitable to maintain or improve the viability of at least a portion of the cells being cultured. One non-limiting example is perfusion of a cell containing tissue or organ in an appropriate media to maintain or improve viability of cells in the tissue or organ. Another non-limiting example is the culturing of cells in a suitable media, such as on a plate or in suspension. While any suitable media may be used, preferred media would have reduced amounts of, or the absence of, agents which interfere with the conversion of a pre-dye to a detectable dye within a viable cell. Non-limiting examples of such an agent include antioxidants and phenol red, which is preferably omitted from culture media, such as those based on Hank's Balanced Salt Solution or Dulbecco's Modified Essential Medium (DMEM), used in the practice of the present invention. Of course culturing may be by use of an suitable device, including incubators, and chambers.

In addition to being cultured, the cells for use in the present invention may also have been otherwise treated in vitro prior to use in the methods of the invention. As non-limiting examples, the cells may have been treated ex vivo, by contact with agents which activate cell growth, agents which activate cells to differentiate one or more further steps toward a terminally differentiated phenotype, or nucleic acid containing agents which transduce the cells. Of course in some embodiments of the invention, the cells are already terminally differentiated or are believed to be terminally differentiated.

In preferred embodiments of the invention, the cells are part of a donor tissue or other cell containing material to be transplanted into a recipient subject. The cells for transplantation may have been originally obtained from the subject into which they are to be transplanted (i.e. autologous transplantation). Cells or tissues that have been cultured or otherwise treated in vitro prior to autologous transplantation may be considered to be ex vivo treated cells or tissues. Alternatively, transplantation may be of a donor tissue or other cell containing material from one subject to another.

Cells for transplantation into patients afflicted with any disease or unwanted condition may be used in the practice of the invention. Non-limiting examples include cells for use in the treatment of a neurodegenerative condition, such as Parkinson's disease, spinal cord injury, multiple sclerosis, Alzheimer's disease, Huntington's disease, hair loss, and natural neuronal degeneration due to aging. Other non-limiting examples include cells for treating diabetes, leukemia, bone marrow transplantation, or hair loss as well as for use in cosmetic or reconstructive surgery.

The instant invention is particularly advantageously used in transplant situations because the number, or relative number, of viable cells in the tissue, or other cell containing material, to be transplanted may be determined based upon determination of viability of a sampling of cells from the tissue (or other cell containing material). This permits a determination of whether the cell containing material (in tissue form or otherwise) is likely to have continued viability, or further metabolic activity, growth and/or proliferation, in vivo after transplantation. Metabolic activity refers to the ability of a cell to continue utilizing energy to maintain homeostasis as well as any enhancement in the redox environment within a cell which converts pre-dye to detectable dye.

The viable cells detected by the present invention are preferably those with a therapeutically advantageous or effective phenotype or function. Non-limiting examples include insulin producing cells, dopamine producing cells, immune system cells, hemopoietic stem cells, and neural cells. Other non-limiting examples include cells for use in in vitro fermentation to produce a protein or nucleic acid product expressed by the cells or other metabolite, such as, but not limited to, steroid hormones, carbohydrates, lipids, etc., of the cells.

As stated above, cells for use in the present invention may or may not be terminally differentiated. Cells that are not terminally differentiated may be viewed as cells that are capable of further differentiation by one or more steps of differentiation. One non-limiting example of such cells is seen with progenitor cells, which are cells that have taken at least one step toward differentiation while retaining the ability to take one or more additional steps. Such cells may have retained a multipotent phenotype. Another non-limiting example is seen with stem cells, which may be multipotent or totipotent but are cells that are precursors to all progenitor cells. Progenitor cells may also be defined as "committed" and "uncommitted" cells which refer to their ability to become less differentiated by restoring the ability to take one or more steps toward differentiation toward a different terminally differentiated outcome.

Additional non-limiting examples of such cells include hematopoietic stem cells, bone marrow cells, umbilical cord blood cells, neural stem cells, neural progenitor cells, adult or embryonic or fetal stem cells, and embryonic stem cells. Non-limiting examples of neural stem or progenitor cells include nestin expressing neuroepithelial cells or radial glial cell-like neuroglial progenitor cells.

Of course the invention may also be practiced with cells derived from any stem or progenitor cell. Such cells may have been derived, or differentiated, during culture in vitro (or ex vivo) in the absence of any intentional stimulation or contact with an exogenous factor or agent. Alternatively, the cells may have been contacted in vitro or ex vivo with an exogenous factor or agent which stimulates differentiation via taking one or more steps toward terminal differentiation.

Non-limiting examples of terminally differentiated cells for use in the present invention include insulin producing cells, such as pancreatic islet cells, dopamine producing cells, hepatocytes, neurons, motor neurons, glial cells, lymphocytes, leukocytes, fibroblasts, skin cells, hair cells, epithelial cells, and oligodendrocytes.

In embodiments of the invention to detect the effects of a test compound or drug on cell viability or the intracellular redox environment, the invention provides a method comprising contacting cells with an amine containing pre-dye simultaneous with or after said cells are contacted with a test compound or drug, wherein said pre-dye is converted to a detectable dye in viable cells; fixing the contacted cells to form fixed cells wherein cells that were viable remain stained by the dye; detecting fixed cells that fluoresce; determining the number, or the relative number, of viable cells based on the number of cells stained with said fluorescent dye; and comparing said number or relative number to another sample of cells not contacted with said test compound or drug. In cases of determining the actual number of viable cells, the cells tested with and without contacting the test compound or drug should be as identical as possible. In cases of determining the relative number, the number of fluorescent cells are compared to the total number of cells in the contacted portion or the number of number of cells that were not stained by the dye.

In preferred embodiments of the invention, the cells are treated with the test compound or drug before being contacted with a pre-dye and processed as described herein. As a non-limiting example, candidate molecules that are to be tested for a potential cytotoxic effect may be placed in contact with cells, optionally over a range of concentrations or amounts in individual applications of the invention, prior to being contacted with a pre-dye and processed as disclosed. Similarly, candidate molecules that are to be tested for a potential effect on the cellular redox environment may be similarly used in the practice of the invention.

Non-limiting examples of test compounds and drugs include growth factors, cytokines, steroid hormones, cell surface binding molecules (e.g. ligands that bind a cell surface receptor), antibodies that bind the cell surface, antitumor agents, anti-proliferative agents, extracts of naturally occurring biological materials, compounds isolated from naturally occurring biological materials, and small organic molecules produced synthetically or isolated from naturally occurring sources. In other preferred embodiments of the invention the test compound or drug is one that may cause oxidative insult to cells, particularly insulin producing cells or dopamine producing neurons.

Of course the ability of a test compound or drug to counteract or alleviate the cytotoxic effect of another agent may also be tested. In such embodiments of the invention, the method comprises contacting cells with an amine containing pre-dye simultaneous with or after said cells are contacted with a test compound or drug and a cytoxic agent, wherein said pre-dye is converted to a detectable dye in viable cells; fixing the contacted cells to form fixed cells wherein cells that were viable remain stained by the dye; detecting fixed cells that fluoresce; determining the number, or the relative number, of viable cells based on the number of cells stained with said fluorescent dye; and comparing said number or relative number to another sample of cells not contacted with said test compound or drug. Of course the cytotoxic agent may be placed in contact with the cells after the contacting with the test compound or drug. This permits the identification of the test compound or drug as having a preventive, or prophylactic effect relative to the cytotoxic agent. Alternatively, the cytotoxic agent may be placed in contact with the cells simultaneously with contacting the cells with the test compound or drug. This permits the identification of the test compound or drug as having a rapid effect in counteracting or alleviating the cytotoxic effect of the agent.

As a non-limiting example, oxidative stress from radicals such as superoxide has been associated with neuronal cell death and neurodegenerative conditions such as Parkinson's disease. Mouse embryonic stem cells (ESCs) have been used to generate dopaminergic neurons deficient in DJ-1 (see Martinat et al. PLoS Biol. 2(11):e327 (2004)). These cells have enhanced sensitivity to oxidative stress and mimic the mutation found in human inherited Parkinson's disease. DJ-1 has also been linked to the aggregation of alpha-synuclein, which is also associated with Parkinson's disease. The present invention may be applied to such mouse ESCs as well as any human or other mammalian cells to identify or screen for new neuroprotectant drugs which modulate or reduce the effects of oxidative stress in the cells. Such use in human ESCs or human adult or fetal stem cells are preferred embodiments of the invention.

As an additional non-limiting example, the effect of an activation agent on cells is contemplated for use with the present invention. Non-limiting activation agents for use with immune system cells include phorbol 12-myristate 13 acetate, ionomycin, Staphylococcal enterotoxin B (SEB), and brefeldin-A.

The invention also provides for a further modification to identify or screen for an agent that causes oxidative insult or injury to a cell. Such an assay to may be helpful in identifying agents with anticancer or antitumor activity.

Of course this embodiment of the invention can also be modified and used in cases of an agent that causes oxidative insult or injury to a cell, such as in an assay to identify anticancer or antitumor agents.

As in the case above, cells tested with and without contacting the test compound or drug should be as identical as possible where determining the actual number of viable cells is used. Where the relative number of cells is determined, the number of fluorescent cells are compared to the total number of cells in the contacted portion or the number of number of cells that were not stained by the dye.

The invention further provides for articles of manufacture to identify or detect viable cells. An article of manufacture according to the present invention may be a kit for the practice of the methods disclosed herein or an article containing one or more reagents needed to practice the methods. The kit can comprise the pre-dye and/or labeled member(s) of a binding pair or specific binding pair and/or fixative and/or permeabilization agent, as well as optionally one or more other reagents, for use in the present invention, together with suitable packaging material. Preferably, the packaging includes a label or instructions for the use of the article or kit in a method disclosed herein.

Having now generally described the invention, the same will be more readily understood through reference to the following examples which are provided by way of illustration, and are not intended to be limiting of the present invention, unless specified.

EXAMPLES

The following examples are offered to illustrate, but not to limit the claimed invention.

Example 1

Materials and Methods

All materials may be obtained from any suitable source, including those available from multiple commercial entities. Many pre-dyes are available from Molecular Probes as well as other vendors.

As an alternative to the following general protocol, the IntraCyte™ Intracellular FACS Kit from Orion Biosolutions (Vista, Calif.) may be used to conduct steps beginning with the fixation step.

General Protocol

For cells that are not normally in suspension, prepare single-cell suspension by enzymatic digestion or dissociation, preferably sufficiently mild to minimize cell damage. As a non-limiting example, adherent cells may be incubated cells with trypsin/EDTA in a buffered salt solution at physiological pH, such as by use of trypsin/EDTA in Hank's Balanced Salt Solution (HBSS) without Ca++/Mg++ or phenol red (Sigma Cat. # H-6648). Trypsin may be present from 0.2 to 0.01% (w/v) while EDTA may be present from 0.02 to 0.001% (w/v) as non-limiting examples.

In cases of organs or tissues, collagenase, at 0.5 to 2 mg/ml in Ca++ containing balanced salt solutions at physiological pH (e.g. DMEM) may be used prior to trypsinization. As a non-limiting example, pancreatic islets may be first liberated from pancreata using a collagenase perfusion, with isolated islets being subsequently trypsinized. Sigma Cat. # T-4174 diluted 25-fold in HBSS may be used for isolated islets at 20 to 28° C. (room temperature) for 20 minutes with occasional mixing, followed by gentle trituration with 5 ml serological pipet.

Trypsin activity may be neutralized by adding an equal volume of protein-containing HBSS (0.1% BSA or 1% serum added). Suspended cells may be centrifuged at approximately 200 g for 5 to 10 minutes, optionally at reduced temperature, to concentrate them.

Of course in cases with cells already in suspension, the above enzymatic steps may be omitted such that only the concentration step, if necessary, is used.

After removal of media, the cells are resuspended. As a non-limiting example, the cells are resuspended in 37° C. pre-warmed DMEM/F12 without phenol red or added protein (Gibco Cat. #21041-025). Preferably, a sample of unstained cells, e.g. about $5 \times 10^4$ as a non-limiting example, are removed at this point for visual inspection or use in FACS to determine the levels of background fluorescence.

All or part of the resuspended cells are contacted with a pre-dye. Alternatively, the pre-dye was present during collagenase perfusion and/or digestion with trypsin. As a non-limiting example, dihydrorhodamine 123 (Molecular probes Cat. # D23806) is added to a final concentration of 1 to 5 μM from a 5 mM stabilized stock. The cells are gently mixed. Optionally, aliquots of the stock pre-dye may be stored as single-use small aliquots at −20° C.

For immediate use, the cells are incubated for 15 to 30 minutes at 37° C. or other suitable temperature. A sample of cells, e.g. about $5 \times 10^4$ as a non-limiting example, may be removed at this point for FACS analysis. In cases with dihydrorhodamine 123, the cells are analyzed with 488 nm excitation in FL1 channel (525 nm band pass filter). This "live" sample analysis is not required, but is helpful to control for loss of non-viable cells after fixation. The unstained sample described above is used to set background fluorescence levels in first decade of log scale in FL1.

The remaining cells are washed, optionally with DMEM/F12 followed by centrifuging/concentration as described above followed by resuspension, such as in 1 ml HBSS as a non-limiting example. The cells may then be fixed with an appropriate fixative, such as one containing formaldehyde. As a non-limiting example, 4 ml of formalin is added to 1 ml of resuspended cells followed by gentle mixing. Fixation is permitted to continue in the dark for any appropriate length of time, such as, but not limited to, at least 3 hours at about 20 to about 28° C. (room temperature), or overnight at 4 to 10° C. in refrigerator.

After fixation, the cells are washed and concentrated again. The cells may be, as a non-limiting example, washed in HBSS or PBS (phosphate buffered saline) by adding at least 3 volumes and centrifuging at 300 to 400 g for 10 minutes at 15 to 25° C.

The wash solution may be used to resuspend the cells, such as in 10 to 15 ml or a larger or smaller volume as appropriate. The wash solution may optionally include a non-ionic detergent as described herein. The wash solution may also be and optionally used to permeabilize the cells where needed or desired by addition of a permeabilization agent. In some embodiments of the invention, the wash or permeabilization times can be short, on the order of about 5 minutes or more, including the time to pellet the cells by centrifugation. However, longer times, up to the order of about 4 weeks or longer is possible provided that the sample is stored properly. For example, storage in the dark is preferred to protect the detergent and dye from photooxidation or bleaching. Most permeabilization agents may be used as known in the art.

The permeabilized cells are then washed and resuspended again in the same or another solution followed by optional addition of a blocking agent prior to contact with a labeled first member of a binding pair.

Controls for the use of the invention with FACS are as follows:
a. Sample untreated with any dye or reagent, for background autofluorescence;
b. Sample treated only with only pre-dye, such as dihydrorhodamine 123, for fluorescence compensation;
c. Sample treated only with labeled first member, such as a primary antibody to detect a cellular molecule on or in the cells, for second color compensation; and
d. Sample treated with dihydrorhodamine 123 and a control (irrelevant) antibody or IgG, for background antibody binding.

Controls a and c are optional, but they are useful in the practice of the invention.

The test samples of cells, after the optional blocking step, are contacted with a labeled first member, such as an antibody to a second member (phenotypic marker of interest). In the case with an antibody, it should be titered to determine optimum signal to noise ratio. A general approximate range however, is from about 0.5 to about 2 µg/ml for most antibodies. As a non-limiting example, Ms×Proinsulin (Novus Biologicals Cat. # AB8305) is used at 0.5 µg/ml. Moreover, and in the case with some antibodies, they may be left unlabeled for subsequent detection with a labeled secondary antibody or an antibody binding reagent, such as protein A.

The labeled first member is preferably incubated with the cells for about 30 to about 60 minutes at room temperature. The cells are then washed and resuspended as described above followed by FACS analysis if the first member is detectably labeled.

Alternatively, and in cases where the use of a detectably labeled antibody is desired (such as with the use of an unlabeled primary antibody or the use of another first member which is bound by the detectably labeled antibody), the cells are optionally blocked as described above followed by contact with the detectably labeled antibody.

As a non-limiting example, a secondary fluorochrome-conjugated antibody is contacted with the cells for about 30 to about 60 minutes to bind the primary antibody. The use of PE-conjugated secondary antibody is preferred. Alternatively, any fluorochrome that can be distinguished from the detectable dye used to determine viability (such as rhodamine 123/FL1 fluorescence on a flow cytometer) can be used. Non-limiting examples include APC or Red-670. PE and similar FL2 fluorochromes are preferred because they are excitable with a 488 nm argon laser and allow for additional FL3 fluorochromes to be used for 3-color analysis (i.e. with a second first member of a binding pair). For example 7AAD for DNA analysis can be combined with both rhodamine 123 and PE.

The treated cells are then washed and resuspended as described above followed by FACS analysis. The FACScan or FACSCalibur (Becton-Dickinson) may be used as non-limiting examples, with Data collected for 10,000 events and analyzed using a Cell Quest program (Becton Dickinson).

Example 2

Intracellular FACS Analysis of Rat Neural Stem Cells

Rat neural stem cells were obtained and treated essentially as described in Example 1. The cells were exposed to retinoic acid and growth factor withdrawal for 5 days followed by contact with dihydrorhodamine. The cells were then fixed and permeabilized followed by contact with a PE conjugated antibody against beta-tubulin III (TuJ1), the expression of which is used to identify a phenotype of differentiating cells.

The results are shown as dual-parameter contour plots in FIG. 1, where the horizontal axes are rhodamine 123 fluoresence and the vertical axes are cell counts. The figure shows the portion of TuJ1-positive neuronal cells (upper quandrants in right panel) in comparison to the use of a PE conjugated IgG (left panel) as a negative control. 15% of total cells were TuJ1 positive as well as rhodamine 123 (RH123) positive and thus were viable. 6.4% of neuronal cells were TuJ1 positive but rhodamine 123 negative or non-viable at the time of assay. Thus the relative number of viable cells with TuJ1 expression can be more accurately determined by eliminating TuJ1 positive cells that were dead. The relative number of viable cells may also be compared to other cell samples or cells treated with other protocols to determine their effects on both viability and TuJ1 expression.

70.3% of total cells were detected as having been viable, but lacked TuJ1 expression, while 8.4% of cells were not viable and lacked expression.

All references cited herein are hereby incorporated by reference in their entireties, whether previously specifically incorporated or not. As used herein, the terms "a", "an", and "any" are each intended to include both the singular and plural forms.

Having now fully described this invention, it will be appreciated by those skilled in the art that the same can be performed within a wide range of equivalent parameters, concentrations, and conditions without departing from the spirit and scope of the invention and without undue experimentation. While this invention has been described in connection with specific embodiments thereof, it will be understood that it is capable of further modifications. This application is intended to cover any variations, uses, or adaptations of the invention following, in general, the principles of the invention and including such departures from the present disclosure as come within known or customary practice within the art to which the invention pertains and as may be applied to the essential features hereinbefore set forth.

What is claimed is:

1. A method of identifying a cell as having been viable and having a phenotype of interest, said method comprising
   contacting a cell with an amine containing pre-dye wherein said pre-dye is converted to a fluorescent dye in viable cells;
   fixing said contacted cell wherein viable cells remain stained by said fluorescent dye;
   optionally treating said fixed cells with a permeabilizing agent;
   contacting said fixed cells with a labeled first member of a binding pair which binds to a second member of the binding pair in or on said fixed cells, wherein presence of said second member is indicative of a cell with a phenotype of interest; and
   identifying said fixed cell as having been viable and having said phenotype by detection of fluorescence from said dye and detection of said labeled first member bound to said second member.

2. The method of claim 1 wherein said second member is an mRNA molecule or a polypeptide.

3. The method of claim 1 wherein said first member of a binding pair is an antibody, optionally attached to a fluorescent label.

4. The method of claim 1 wherein said first member of a binding pair is a nucleic acid molecule or a nucleic acid binding dye.

5. The method of claim 1 wherein said first member of a binding pair is labeled for indirect detection.

6. The method of claim 5 wherein said first member of a binding pair is labeled with biotin.

7. The method of claim 1 wherein said first member of a binding pair is detectably labeled.

8. The method of claim 1 wherein said identifying is by use of two channel fluorescent activated cell sorting (FACS).

9. The method of claim 1 wherein said cell has been previously subjected to an isolation procedure or treatment.

10. The method of claim 9 wherein said isolation procedure is surgical isolation or enzymatic dissociation.

11. The method of claim 1 wherein said second member of the binding pair is expressed inside said cell.

12. The method of claim 1 wherein said cell is a pancreatic islet cell and said second member of the binding pair is insulin.

13. The method of claim 1 wherein said pre-dye is converted to a detectable dye by a reactive oxygen species (ROS) in viable cells.

14. The method of any previous claim wherein said pre-dye is non-fluorescent dihydrorhodamine 123, MTT or XTT.

15. The method of claim 1 wherein said phenotype of interest is a expression of a gene product of interest or the presence of a pathogen.

16. The method of claim 1 wherein said fixing is with a fixative comprising an aldehyde.

17. The method of claim 1 wherein said fixative comprises formaldehyde or formalin.

18. A method of determining the relative number of viable cells having a phenotype of interest from within a population of cells, said method comprising contacting a portion of said population of cells with an amine containing pre-dye wherein said pre-dye is converted to a fluorescent dye in viable cells;

fixing said contacted portion of said population of cells to form fixed cells wherein viable cells that have been fixed are stained by said fluorescent dye;

optionally treating said fixed cells with a permeabilizing agent;

contacting said fixed cells with a labeled first member of a binding pair which binds to a second member of the binding pair in or on said fixed cells, wherein presence of said second member is indicative of a cell with a phenotype of interest; and determining the relative number of viable cells having said phenotype in said portion, as a representative sample of said population of cells, based on the number of cells stained with said fluorescent dye and based on the number of cells stained with said fluorescent dye and bound by the labeled first member via the second member in or on the cells, in comparison to the total number of cells in said portion.

19. The method of claim 1 wherein said pre-dye is non-fluorescent dihydrorhodamine 123.

20. The method of claim 7 wherein said first member of a binding pair is fluorescently labeled.

* * * * *